United States Patent [19]
Chan et al.

[11] Patent Number: 5,827,654
[45] Date of Patent: Oct. 27, 1998

[54] BASAL BODY ROD PROTEIN GENES OF CAMPYLOBACTER

[75] Inventors: Voon Loong Chan, Toronto; Helena Louie, Markham, both of Canada

[73] Assignee: University of Toronto, Toronto

[21] Appl. No.: 436,748

[22] Filed: May 8, 1995

[51] Int. Cl.[6] .................................................. C12Q 1/68
[52] U.S. Cl. ............................................ 435/6; 424/271.1
[58] Field of Search ............................... 435/6; 424/271.1

[56] References Cited

U.S. PATENT DOCUMENTS

| | | | |
|---|---|---|---|
| 4,258,029 | 3/1981 | Moloney et al. | 424/271.1 |
| 4,596,792 | 6/1986 | Vyas | 514/21 |
| 4,599,230 | 7/1986 | Milich et al. | 424/189.1 |
| 4,599,231 | 7/1986 | Milich et al. | 424/189.1 |
| 4,601,903 | 7/1986 | Frasch | 424/250.1 |
| 4,855,283 | 8/1989 | Lockhoff et al. | 424/278.1 |
| 4,952,496 | 8/1990 | Studier et al. | 435/91.41 |
| 5,494,795 | 2/1996 | Guerry et al. | 435/6 |

OTHER PUBLICATIONS

Penner J.L., (1988) Clin. Microbiol. Rev. 1: 157–172.
Macnab, Robert M. (1992) Annu. Rev. Genet. 26: 131–158.
Aizawa, S. et al., J. Bact. 161 (3), 1985, 836–849.
Komeda, Y. et al., J. Bacteriol. 134: (1978) 655–677.
Homma M. et al., J. Bacteriol. 169: (1987) 3617–3624.
Homma M. et al., J. Biol. 211: (1990) 465–477.
Kazuhiro et al., J. Bacteriol. 176: (1994) 3598–3605.
Nuijten, P.J.M. et al, J. Biol. Chem. 265: 29 (1990) 17798–17804.
Fisher S.H. and Nachamkim, I., (1991) Mol. Microbiol. 5: 1151–1158.
Khawaja, R. et al., Current Microbiol. 24: (1992) 213–221.
Chan, V.L. et al., Gene 73: (1988), 185–191.
Homma M. et al., J. Miol. Biol. 213: (1990) 819–832.
Albertini. A.M. et al., J. Bacteriol. 173 (1991) 3573–3579.
Dingwall. A. et al., J. Mol. Biol. 228: (1992) 1147–1162.
O'Hagan (1992) Clin Pharmokinet. 22(1):1–10.
Ulmer et al., (1993) Curr. Opinion Invest. Drugs. 2(9): 983–989.
Nixon–George et al., (1990) J. Immunol. 144:4798–4802.
Weismuller et al., (1989) Vaccine 7:29–33.
Deres et al., (1989) Nature 342:561–564.
Chang et al., (1978) Nature 275:617–624.
Itakura et al., (1977) Science 198:1056–1063.
Goeddel et al., (1979) Nature 281:544–548.
Goeddel et al., (1980) Nucl. Acids Res. 8:4057–4074.
Henikoff, S., Gene 28: (1984) 351–359.
Hawley, D.K. et al., Nucl. Acid Res. 11: (1983) 2237–2255.
Benhar, et al. Mol. Microbiol. 6(19): 2777–2784.
Curran, J.F., Nucl. Acid. Res. 21(8): (1993) 1837–1843.
Clare, J.J. et al., Proc. Natl. Acad. Sci. 85: (1988) 6816–6820.
Yelverton, E. et al., Microbiol. 11(2): (1994) 303–313.
Brierley, I. et al., Cell 57: (1989) 537–547.
Chandler, M. et al., Mol. Microbiol. 7: (1993) 497–503.
Sancer, B. et al., J. Bacteriol. 137: (1979) 692–693.
Roger Lewin, Science, vol. 237, p. 1570, 1987.
Reeck, GR et al, Cell, vol. 50, p. 667, Aug. 28, 1987.
Kin, N.W et al, Journal of Bacteriology, NOv. 1993, pp. 7468–7470, vol. 175(22).
Orkin, S.H. et al, Dec. 7, 1995, Report and Recommendations of the panel to assess the NIH investment in research on gene therapy.

*Primary Examiner*—James C. Housel
*Assistant Examiner*—Ginny Allen Portner
*Attorney, Agent, or Firm*—Sim & McBurney

[57] ABSTRACT

Purified and isolated nucleic acid molecules are provided which encode a basal body rod protein of a strain of Campylobacter, particularly *C. jejuni*, or a fragment or an analog of the basal body rod protein. The nucleic acid molecules may be used to produce proteins free of contaminants derived from bacteria normally containing the FlgF or FlgG proteins for purposes of diagnostics and medical treatment. Furthermore, the nucleic acid molecules, proteins encoded thereby and antibodies raised against the proteins, may be used in the diagnosis of infection.

12 Claims, 9 Drawing Sheets

```
         10         20        30        40        50       60
   TCTCCTAATAATCTTTCAAATATTTATTTTTCTTTGTTTTTAAAAGTTGGAACACTCTTTG...

70        80        90       100       110       120
          ...CTTTTATAGTTATAAAATCTTAAATTTATAGGTGAAAATATGCAAAATGGATATTATCA
                                                          M  Q  N  G  Y  Y  Q 130       140       150       160       170       180
    AGCAACTGGCGGAATGGTAACTCAGTTTAATAAACTTGATGTGATTACTAATAATCTTGCC...
     A  T  G  G  M  V  T  Q  F  N  K  L  D  V  I  T  N  N  L  A 190       200       210       220       230       240
          ...AATATCAATACAAGTGGATATAAAAGAGATGATGTGGTTATTGCAGATTTTAAAAGGAT
              N  I  N  T  S  G  Y  K  R  D  D  V  V  I  A  D  F  K  R  I 250       260       270       280       290       300
    TTTTAAAGAAACTCAGGATGAGTTGCCTATAGAAAATCACACAAGAGATGCATCTCGTTTT...
     F  K  E  T  Q  D  E  L  P  I  E  N  H  T  R  D  A  S  R  F 310       320       330       340       350       360
          ...GTAAATACTACAATAGATGGAATCCCACAAGTTTCTCAAGAATATACGGATTTTAGCCT
              V  N  T  T  I  D  G  I  P  Q  V  S  Q  E  Y  T  D  F  S  L 370       380       390       400       410       420
    AGGTTCTTTAAAGGCCACAAACAATCCTTTGGATTTGGCAATGACTAGAGAAGATGCTTTT...
     G  S  L  K  A  T  N  N  P  L  D  L  A  M  T  R  E  D  A  F
```

FIG.1A

```
          10         20         30         40         50         60
TCTCCTAATAATCTTTCAAATATTTATTTTTCTTTGTTTTTAAAAGTGTGGAACACTCTTTG...

70         80         90        100        110        120
...CTTTTATAGTTATATAAAATCTTAAATTTATAGGTGAAAATATGCAAAATGGATATTATCA
                                              M  Q  N  G  Y  Y  Q 130        140        150        160        170        180
AGCAACTGGCGGAATGGTAACTCAGTTTAATAAACTTGATGTGATTACTAATAATCTTGCC...
 A  T  G  G  M  V  T  Q  F  N  K  L  D  V  I  T  N  N  L  A 190        200        210        220        230        240
...AATATCAATACAAGTGGATATAAAAGAGATGATGTGGTTATTGCAGATTTTAAAAGGAT
    N  I  N  T  S  G  Y  K  R  D  D  V  V  I  A  D  F  K  R  I 250        260        270        280        290        300
TTTTAAAGAAACTCAGGAGAGTGCCTATAGAAAATCACACAAGAGATGCATCTCGTTTT...
 F  K  E  T  Q  D  E  L  P  I  E  N  H  T  R  D  A  S  R  F 310        320        330        340        350        360
...GTAAATACTACAATAGATGGAATCCCACAAGTTTCTCAAGAATATACGGATTTTAGCCT
    V  N  T  T  I  D  G  I  P  Q  V  S  Q  E  Y  T  D  F  S  L 370        380        390        400        410        420
AGGTTCTTTAAAGGCCACAAACAATCCTTTGGATTTGGCAATGACTAGAGAAGATGCTTTT...
 G  S  L  K  A  T  N  N  P  L  D  L  A  M  T  R  E  D  A  F
```

FIG. 1B

```
                     430              440              450              460              470              480
       ...TATTTGGTTCAGACCAAAGATGGAGAAGTAAGATTAACCAAAGATGGAAATTTTCAACT
          Y  L  V  Q  T  K  D  G  E  V  R  L  T  K  D  G  N  F  Q  L 490              500              510              520              530              540
TGATGATGAGGGTTATTTGGTAAATAAGCAAGGATACAAGGTATTAAGTAGTGATTATTTT...
 D  D  E  G  Y  L  V  N  K  Q  G  Y  K  V  L  S  S  D  Y  F 550              560              570              580              590              600
       ...AATAATCCTCAGAATGCTGGCATACGCATTCCTAATAGTGCTGTTCAAATTAGCGTTGA
          N  N  P  Q  N  A  G  I  R  I  P  N  S  A  V  Q  I  S  V  D 610              620              630              640              650              660
TAAAAACGGAAGCATTGAAGTTGATGGAGCTCAAAATGCAAGATTATTTGTAGCACAAGTA...
 K  N  G  S  I  E  V  D  G  A  Q  N  A  R  L  F  V  A  Q  V 670              680              690              700              710              720
       ...GATGATATAAGAGCTTTGCAAAAAGATGGGGATAATGTCTATAAAATAGATGATCTAAC
          D  D  I  R  A  L  Q  K  D  G  D  N  V  Y  K  I  D  D  L  T 730              740              750              760              770              780
CCGTATTAGAGAGATTTGAAAAACTCCAATGCTATTCGCCAAGTTTTTCCTCAGGGATCAAAT...
 R  I  R  D  L  K  N  S  N  A  I  R  Q  G  F  S  Q  G  S  N 790              800              810              820              830              840
       ...GTTAATCCAGTTACTGAAATGGTTAGGACTGAAGCAAACAGAATGGTAGAAATGTA
          V  N  P  V  T  E  M  V  G  L  I  E  A  N  R  M  V  E  M  Y
```

FIG. 1C

```
      850         860         870         880         890         900
TCAAAAAGTTATGACAGCTCCATATGGATGACTTAAATCAAGAAGCTATCAATAAGCTTGCA...
 Q   K   V   M   T   A   H   M   D   D   L   N   Q   E   A   I   N   K   L   A 910         920         930         940         950         960
...GCTGTTAAATAATTTAAAATAAAATAAAAAGGATTAAAAAATGATGAGATCACTTCATA
   A   V   K                                    M   M   R   S   L   H 970         980         990         1000        1010        1020
CTGCTGCTACAGGAATGGTAGCCGCAGCAAACACAAATTGATGTTACTTCAAATAACATCGC...
 T   A   A   T   G   M   V   A   Q   Q   T   Q   I   D   V   T   S   N   N   I   A 1030        1040        1050        1060        1070        1080
...CAATGTTAATACAGCAGGTTTTAAGAAAAGTCGCGCAGAATTTGCTGATCTTATGTATC
   N   V   N   T   A   G   F   K   K   S   R   A   E   F   A   D   L   M   Y 1090        1100        1110        1120        1130        1140
AAGTTATGAAGTATGCAGGAACTTCAACTTCAGCTACTACTCTTTCTCCTTCGGGTATAGA...
 Q   V   M   K   Y   A   G   T   S   T   S   A   T   T   L   S   P   S   G   I   E 1150        1160        1170        1180        1190        1200
...AGTGGGTGTGGGTGTGCGTCCAACAGCGGTAACTAAAAGTTTTTACTGAAGGAAATTTAA
   V   G   V   G   V   R   P   T   A   V   T   K   V   F   T   E   G   N   L
```

FIG.1D

```
       1210        1220        1230        1240        1250        1260
AATCAACAAGTACTGATGGTCTTGATATGGCTATTGCAGGTAATGGGTTTTTCAAATACA...
 K  S  T  T  D  G  L  D  M  A  I  A  G  N  G  F  F  Q  I  Q 1270        1280        1290        1300        1310        1320
       ...ACTTCCTGATGGCACTATAGAAATGGGCAATTTACAAAAGATAATGAAGGATAATGAAG
           L  P  D  G  T  I  G  Y  T  R  N  G  Q  F  T  K  D  N  E 1330        1340        1350        1360        1370        1380
GTAATATTGTAAATTCAGATGGTTATAGACTTTTACCTGAAATGACAATACCTGAAGGCGC...
 G  N  I  V  N  S  D  G  Y  R  L  L  P  E  M  T  I  P  E  G  A 1390        1400        1410        1420        1430        1440
       ...AACAGCAATTAATGTTGCTACAGATGGAACCGTTTCTGTAATGCTACCAGGGGAGCAAC
           T  A  I  N  V  A  T  D  G  T  V  S  V  M  L  P  G  E  Q 1450        1460        1470        1480        1490        1500
AAGAAACTCAAATTGGCCAAGTGGAGCTAGTTCAGTTTTATAAATCCAGCGGGTCTTCATTC...
 Q  E  T  Q  I  G  Q  V  E  L  V  Q  F  I  N  P  A  G  L  H  S 1510        1520        1530        1540        1550        1560
       ...TATGGGTGATAATCTTTATCTTGAAACAGGAGCAAGTGGTGCACCTGTTGCGGGTATAG
           M  G  D  N  L  Y  L  E  T  G  A  S  G  A  P  V  A  G  I
```

FIG.1E

```
      1570       1580       1590       1600       1610       1620
CAGGACAAGATGGGCTTGATGAACAATAAGAGACATGGATTTATAGAACTTAGTAATGTTCAGCT...
 A  G  Q  D  G  L  G  T  I  R  H  G  F  I  E  L  S  N  V  Q  L 1630       1640       1650       1660       1670       1680
...TGTTGAAGAAATGACAGATCTTATCACAGGACAAAGAGCTTATGAAGCGGGTTCTAAGG
    V  E  E  M  T  D  L  I  T  G  Q  R  A  Y  E  A  G  S  K 1690       1700       1710       1720       1730       1740
CCATTACAACAAGTGATGATATGCTAGGAATTGTAAATCAGCTTAAGCGATAGTTGATATA...
 A  I  T  T  S  D  D  M  L  G  I  V  N  Q  L  K  R 1750       1760       1770       1780       1790       1800
...AAATAAATAATTTTTAATTCTTTTTTGTTAATGGCCGTGTTAAACGCCATTAAATTTTT
```

FIG. 2A

FLGF

```
CJ  MQNGYYQAIGMVTQFNKLDVTINLANINTSGYKRDMVIADFKRIFKEIQDELPIENHTRDASRFVNITIDGIPQVSQ
CC  :D:AL:VGLSRQM:VRRE::IVA::I::A::T:F:VE:IMV    :T EQAKPAKTLDG S SPVK::  :  :V R  R
ST      AI:T:M:AASQTLNQQA:TAS:::AS:P:F :AQ  LNAL :A VPV :G:SLA  ::  T  L:TASTP :: AIMTP

CJ  EYIDFSLGSLKATNNPIDLAMTREDAFYLVQTKDGEVRLTKDGNFQLDEGYLMKQGYKVLSSD YFNNPQNAGIRIFN
CC  NF:Q    :PMTK:GGDY:::IN GMG:FK::ANG::  :Y:R::R:TINP::I::TQA:AP::D :   GGG:IT  :D ;R
ST  GQLDYT  S   R    P::V:L QQ::GMLV: :AA::AEGY:RN:NI::VGPT: QLTI::HP: IGEGGPITV:EGSE:T::AA

CJ  SAVQISVDKNGSIEVDGAQNARLFVAQVDDIRALQKDGDNVYKIDDLTRI R D LKNSNAIR   QGFSQGSNMNPVIEM
CC  LG PVT:G:D:IVSQGAIRVS:IGLVRP::LSTFA::::L:RNTIN:AP Q P VTDAQ :H  ::MLEA:::Q::I:I
ST  DGT  ::AINP:DPPNTV:PVGR:KLVKAEG NEV:RSD:GLFRLTAEFAQAE:GAV:AADPS:: IMS:VLE:::K::EA:

CJ  VGLIEANRMVEMYQKVMTAHMDDLNQ EA I NKLAAVK
CC  TK:::IQ:AY:SVA:M: DNTAE:SRIPSSWARSTRER
ST  IDM:ANA:RF::QM::I:S V:E :E GR A :Q:LSMS
```

FIG. 2B

FLGG

```
CJ    MRSLHTAATGMVAQQIQIDVTSNIANVNTAGFKKSRAFFADLMYQMKYAGR STSATTLSPSGIEWGVGVRPTACTK
CC    : QA:R::S::A:::INVE:I::::::M::V::::RQ::::Q::L::TIERA:SQ:S:DGNIVPT:VQ::G::KAGS:YR
ST    ::IS::WI:K::LD:::TNM::IA::L::S:N:T:RQ::V:E::L::TIRQP:AQ:SEQ:::  :::LQI:T:::VATER
BS    .:L:::YSGIS:GRNF:TKL:::IG::::::V:::::VT:K:MVS:TIA G:S AAG::IGGINSKQI:L:SSSGTIDT

CJ    VFTEGNLKSTSITGLDMAIAGNGFFQIQLPDGTIGYTRNGQFTKDNEGNIVNSDGYR L L PE MTIPEGATAINVAID
CC    I ::QGTPTLIDSP::L::Q:K:YMP:L::S:ETA:::A:N:SINDQ:Q::TE:::L V Q ::G I:::QN::D:TISKS
ST    LHSQ::L :QINNSKDV:IK:Q::::VM::::SA:::D:S:GV:GN:QL:TAG:FQ V Q :A I::AN:LS:TIGR:
BS    IHSTSATQ:TGRT :L::D:Y:R:DTG:::  A::A:N:YL:NT:TL:TG:SYHV:NMNGTIK::TD:QSFSIGS::

CJ    GIVSVMLPGEQQEIQIGQVELVQFINPAGLHSMGDNLYLETIGASGAPVAGI AGQDGLGTIRHGFTELSNVQLVEHMTDL
CC    :L:Q:K:D:QP:PQTV::IQ:AN:L:EG::EAIG::F::A::::ATLVR RASRA:ACCSTDT:A:::DA:S:I:A:
ST    :V:::TQQ:QAAPV:V::IN:TT:M:DT::ESI:E:::I::QS::::NEST P:LN:A:LLYQ:YV:T::NVA::LVNM
BS    SK::IV DA:GKTQDG::IGI:T:A:SD::DKI:S:::R:SIN::TAS:ANQP:DG:T:ALKS::L:N::D:TD:F:EM
```

```
CJ    ITGQRAYEAGSKAITTSDDMLGIVNQLKR
CC    ::A:::::MN::V:S:A:Q::QATS::RS
ST    :QV::::::IN::AVS:T:Q::QKLT::
BS    :VA::GFQSN::I:::::EI:QELVN:::
```

BASAL BODY ROD PROTEIN GENES OF CAMPYLOBACTER

FIELD OF INVENTION

The present invention is related to the molecular cloning of genes encoding basal body rod proteins of flagella and in particular to the cloning of basal body rod protein encoding genes from Campylobacter.

BACKGROUND OF THE INVENTION

*Campylobacter jejuni* is a Gram-negative spiral microaerophilic bacterium that has been recognized as a cause of secretory type diarrhea and enteritis (Ref No. 1. Throughout this application, various references are referred to in parenthesis to more fully describe the state of the art to which this invention pertains. Full bibliographic information for each citation is found at the disclosed end of the specification immediately preceding the claims. These references are hereby incorporated by reference into the present disclosure). The flagellum of *C. jejuni* is responsible for bacterial motility which enhances the organism's pathogenicity. The flagellum consists of three major components; the filament, the hook, and the basal body (ref. 2). These structural components of the flagellum have been extensively studied in *Escherichia coli* and *Salmonella typhimurium* (Refs 3, 4). The basal body is arranged as protein rings and rods embedded in the membrane of the bacteria (Refs 3, 5, 6) and is responsible for transmitting motor functions to the filament via the hook. The majority of the basal body protein genes exist in clusters and are classified as class 2 flagellar operons subject to regulation by the class 1 flagellar genes (Ref 7).

In *C. jejuni*, the flagellin genes, flaA and flaB, encoding the monomeric proteins of the filament have been isolated and sequenced (Refs. 8, 9, 10, 11). However, prior to the present invention, genes for the basal body and hook proteins of *C. jejuni* had not been isolated and characterized. In Salmonella and *E. coli* disruption of these genes resulted in the loss of motility due to the lack of attachment of the filament (Refs. 2, 3). The immotile bacteria were less virulent than the motile counterpart.

Genes encoding the flagellar basal body proteins of *E. coli, S. typhimurium, Bacillus subtilis,* and *Caulobacter crescentus* have been identified and appear as gene clusters within the genome (Refs 12, 13, 14).

It would be advantageous to provide nucleic acid molecules encoding basal body proteins of flagella for strains of Campylobacter and purified basal body proteins including FlgF and FlgG proteins for use as antigens, immunogenic compositions, including vaccines, carriers for other antigens and immunogens and the generation of diagnostic reagents.

SUMMARY OF THE INVENTION

The present invention is directed towards the provision of purified and isolated nucleic acid molecules encoding a basal body rod protein of a strain of Campylobacter or a fragment or an analog of the basal body rod protein. The nucleic acid molecules provided herein are useful for the specific detection of strains of Campylobacter, and for diagnosis of infection by Campylobacter. The purified and isolated nucleic acid molecules provided herein, such as DNA, are also useful for expressing the flgF and flgG genes by recombinant DNA means for providing, in an economical manner, purified and isolated basal body rod proteins, subunits, fragments or analogs thereof. The basal body rod protein, subunits or fragments thereof or analogs thereof, as well as nucleic acid molecules encoding the same and vectors containing such nucleic acid molecules, are useful in immunogenic compositions against diseases caused by Campylobacter, the diagnosis of infection by Campylobacter and as tools for the generation of immunological reagents. Monoclonal antibodies or mono-specific antisera (antibodies) raised against the basal body rod protein produced in accordance with aspects of the present invention are useful for the diagnosis of infection by Campylobacter, the specific detection of Campylobacter (in for example in vitro and in vivo assays) and for the treatment of diseases caused by Campylobacter.

Peptides corresponding to portions of the basal body rod protein or analogs thereof are useful immunogenic compositions against disease caused by Campylobacter, the diagnosis of infection by Campylobacter and as tools for the generation of immunological reagents. Monoclonal antibodies or antisera raised against these peptides, produced in accordance with aspects of the present invention, are useful for the diagnosis of infection by Campylobacter, the specific detection of Campylobacter (in, for example, in vitro and in vivo assays) and for use in passive immunization as a treatment of disease caused by Campylobacter.

In accordance with one aspect of the present invention, there is provided a purified and isolated nucleic acid molecule encoding a basal body rod protein of a strain of Campylobacter, more particularly, a strain of *Campylobacter jejunis*, or a fragment or an analog of the basal body rod protein.

In one preferred embodiment of the invention, the nucleic acid molecule may encode the FlgF protein of the Campylobacter strain or the FlgG protein of the Campylobacter strain. In another preferred embodiment of the invention, the nucleic acid may encode a fragment of the basal body rod protein of a strain of Campylobacter having a conserved amino acid sequence which is conserved among bacteria that produce basal body rod protein. Such conserved amino acid sequence may have an amino acid sequence contained within the amino acid sequences of FIG. 2 for *Campylobacter jejunis* as well as corresponding amino acid sequences of other strains of Campylobacter.

In another aspect of the present invention, there is provided a purified and isolated nucleic acid molecule having a DNA sequence selected from the group consisting of (a) the entire DNA sequence set out in FIG. 1 (SEQ ID No: 1), the DNA sequence of the flgF gene (SEQ ID No: 2), the DNA sequence of the flgG gene (SEQ ID No: 3) or the complementary DNA sequence of any one of said sequences; (b) a DNA sequence encoding the amino acid sequence of the amino acid sequence of the FlgF protein (SEQ ID No: 4), a DNA sequence encoding the FlgG protein (SEQ ID No: 5) or the complementary DNA sequence thereto;

and (c) a DNA sequence which hybridizes under stringent conditions to any one of the DNA sequences defined in (a) or (b). The DNA sequence defined in (c) preferably has at least about 90% sequence identity with any one of the DNA sequences defined in (a) and (b).

In an additional aspect, the present invention includes a vector adapted for transformation of a host, comprising a nucleic acid molecule as provided herein. The vector may be one having the characteristics of plasmids pBSX6, pUH4 or pBSd43.

The plasmids may be adapted for expression of the encoded basal body rod protein, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the basal body rod protein or the fragment or analog of the basal body rod protein. In specific embodiments of this aspect of the invention, the nucleic acid molecule may encode substantially all the FlgF and FlgG proteins, only the FlgF protein or only the FlgG protein of the Campylobacter strain. The expression means may include a nucleic acid portion encoding a leader sequence for secretion from the host of the basal body rod protein or the fragment or the analog of the basal body rod protein. The expression means also may include a nucleic acid portion encoding a lipidation signal for expression from the host of a lipidated form of the basal body rod protein or the fragment or the analog of the basal body rod protein. The host may be selected from, for example, *Escherichia coli*, Bacillus, Haemophilus, fungi, yeast or baculovirus and Semliki Forest virus expression systems may be used.

In an additional aspect of the invention, there is provided a transformed host containing an expression vector as provided herein. The invention further includes a recombinant basal body rod protein or fragment or analog thereof producible by the transformed host. Further aspects of the present invention provide an isolated and purified basal body rod protein of a Campylobacter strain substantially free from other proteins of the Campylobacter strain, an isolated and purified FlgF protein of a strain of Campylobacter free from the FlgG protein of the Campylobacter strain and an isolated and purified FlgG protein of a strain of Campylobacter free from the FlgF protein of the Campylobacter strain. The Campylobacter strain may be *C. jejuni*.

The present invention further provides synthetic peptides corresponding to portions of the basal body rod protein. Accordingly, in a further aspect of the invention, there is provided a synthetic peptide having no less than six amino acids and no more than 150 amino acids and containing an amino acid sequence corresponding to a portion only of a basal body rod protein of a strain of Campylobacter or of a fragment or an analog of the basal body rod protein.

The peptides provided herein may comprise an amino acid sequence which is conserved among bacteria that produce basal body rod protein.

In accordance with another aspect of the invention, an immunogenic composition is provided which comprises at least one active component selected from at least one nucleic acid molecule as provided herein, at least one recombinant protein as provided herein, at least one of the purified and isolated basal body rod proteins, including FlgF or FlgG proteins, as provided herein and at least one synthetic peptide as provided herein, and a pharmaceutically acceptable carrier therefor or vector therefor. The at least one active component produces an immune response when administered to a host.

The immunogenic compositions provided herein may be formulated as a vaccine for in vivo administration to protect against diseases caused by bacterial pathogens that produce basal body rod proteins. For such purpose, the compositions may be formulated as a microparticle, capsule, ISCOM or liposome preparation. Alternatively, the compositions may be provided in combination with a targeting molecule for delivery to specific cells of the immune system or to mucosal surfaces. The immunogenic composition may comprise a plurality of active components to provide protection against disease caused by a plurality of species of basal body rod protein producing bacteria. The immunogenic compositions may further comprise an adjuvant.

In accordance with another aspect of the invention, there is provided a method for inducing protection against infection or disease caused by Campylobacter or other bacteria that produce basal body rod protein, comprising the step of administering to a susceptible host, such as a human, an effective amount of the immunogenic composition as recited above.

In accordance with another aspect of the invention, an antiserum or antibody specific for the recombinant protein, the isolated and purified basal body rod proteins, including FlgF or FlgG protein, synthetic peptide or the immunogenic composition, is provided.

In a further aspect, there is provided a live vector for delivery of basal body rod protein to a host, comprising a vector containing the nucleic acid molecule as described above. The vector may be selected from Salmonella, BCG, adenovirus, poxvirus, vaccinia and poliovirus. The nucleic acid molecule may encode a fragment of the basal body rod protein of a Campylobacter strain which is conserved among bacteria that produce the basal body rod protein. Such vector may be included in an immunogenic composition provided herein.

The present invention further includes a method of determining the presence of nucleic acid encoding the basal body rod protein of a strain of Campylobacter, in a sample, comprising the steps of: (a) contacting the sample with the nucleic acid molecule provided herein to produce duplexes comprising the nucleic acid molecule and any said nucleic acid molecule encoding the basal body rod protein of Campylobacter present in the sample and specifically hybridizable therewith; and (b) determining production of the duplexes.

In an additional aspect, the present invention provides a method of determining the presence of a basal body rod protein of a Campylobacter strain in a sample, comprising the steps of (a) immunizing a subject with the immunogenic composition provided herein to produce antibodies specific for the basal body rod protein; (b) contacting the sample with the antibodies to produce complexes comprising any basal body rod protein of a Campylobacter strain present in the sample and the basal body rod protein specific antibodies; and determining production of the complexes.

A further aspect of the present invention provides a diagnostic kit for determining the presence of nucleic acid encoding the basal body rod protein of a strain of Campylobacter, in a sample, comprising (a) the nucleic acid molecule provided herein; (b) means for contacting the nucleic acid with the sample to produce duplexes comprising the nucleic acid molecule and any said nucleic acid present in the sample and hybridizable with the nucleic acid molecule; and (c) means for determining production of the duplexes.

In another aspect of the present invention, there is provided a diagnostic kit for detecting the presence of a basal body rod protein of a Campylobacter strain in a sample, comprising (a) a basal body rod protein specific antibody to the immunogenic composition provided herein; (b) means for contacting the antibody with the sample to produce a complex comprising said basal body rod protein and the antibody; and (c) means for determining production of the complex.

BRIEF DESCRIPTION OF DRAWINGS

The present invention will be further understood from the following description with reference to the drawings in which:

FIGS. 1A to 1E show the nucleotide sequence of flgFG operon (SEQ ID No: 1). The flgF and flgG coding regions (SEQ ID No: 2 and 3) are shown from nt 101 to 910 and nt 942 to 1730, respectively, with amino acids below (SEQ ID Nos: 4 and 5). The termination codons are underlined. The ribosomal binding sites are denoted by broken lines above the sequence. The class I promoter sequences are denoted by horizontal lines above the sequence, and the class II promoter sequence is indicated by a horizontal line below the sequence. The transcriptional sites are marked by bent arrows.

FIGS. 2A and 2B contain the amino acid sequence homology comparison of FlgF and FlgG proteins among bacteria. The *C. jejuni* sequences (SEQ ID Nos: 4 and 5), CJ, are derived from the nucleotide sequence of FIG. 1. The *Caulobacter crescentus* sequences (CC) (SEQ ID Nos: 6 and 7) are from ref. 14. The *Bacillus subtilis* sequence (BS) (SEQ ID No: 8) is from ref. 13 and ref. 27. The *Salmonella typhimurium* (ST) sequences (SEQ ID Nos: 9 and 10) are from ref. 12. The amino acid sequences are in single letter codes. The sequences were aligned by the Cluster V multiple sequence alignment program and the conserved regions in the amino acid sequences are indicated by double lines above the sequence.

GENERAL DESCRIPTION OF THE INVENTION

Figure 3:
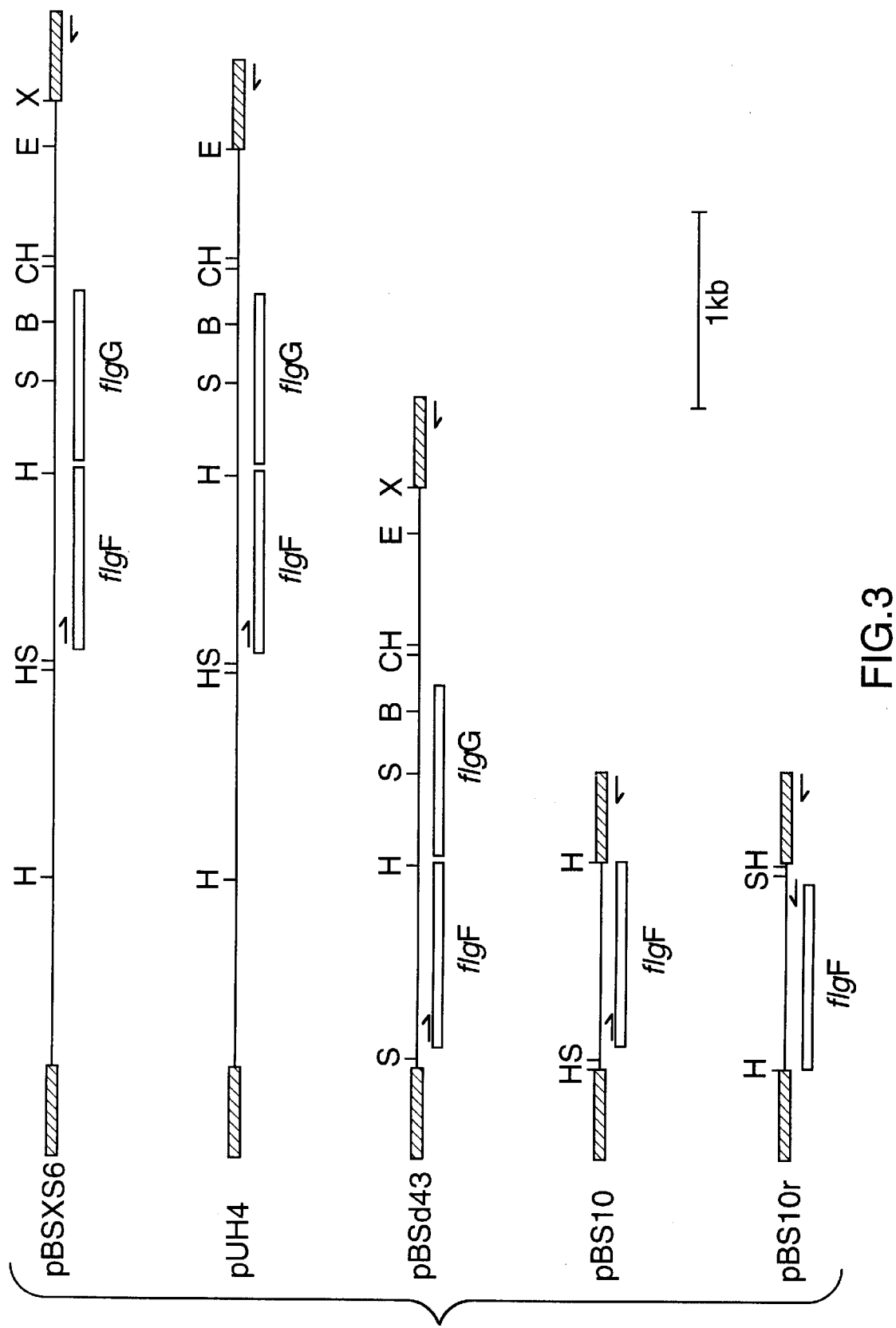
FIG. 3 contains the restriction map of clones pUH4, pBSXS6, pBSd43, pBS10 and pBS10r in pBluescript vector. The location of flgF and FlgG are denoted by the boxed area below the restriction map. The restriction sites are: B,BglII; C, ClaI; E, EcoRI, H, HindIII, S, SspI; and X, XbaI. The shaded boxes represent vector sequences. The direction of transcription is indicated by the arrow.

Any Campylobacter strain may be conveniently used to provide the purified and isolated nucleic acid, provided herein which may be in the form of DNA molecules, comprising at least a portion of the nucleic acid coding for a basal body rod protein of a flagellum as typified by embodiments of the present invention. Such strains are generally available from clinical sources and from bacterial culture collections, such as the American Type Culture Collection, Rockville, Md. U.S.A. One particular useful species is *C. jejuni*.

In this application, the term "basal body rod protein" is used to define a family of FlaF and/or FlaG proteins which includes those having variations in their amino acid sequences including those naturally occurring in various strains of Campylobacter. The purified and isolated DNA molecules comprising at least a portion coding for the basal body rod protein of the present invention also include those encoding functional analogs of the basal body rod protein. In this application, a first protein or peptide is a "functional analog" of a second protein if the first protein is immunologically related to and/or has the same function as the second protein or peptide. The functional analog may be, for example, a fragment of the protein or a substitution, addition or deletion mutant thereof.

Sequence analysis of a false positive clone (pBHL-15) produced on screening the *C. jejuni* TGH9011 recombinant pBR322 library (Ref. 11) with a mixed oligonucleotide probe for the enterotoxin gene of *C. jejuni*, indicated that the plasmid contained a gene with homology to the flgG basal body rod protein of *Salmonella typhimurium* (Ref. 12). Screening of the *C. jejuni* TGH9011 genomic pBluescript library with the 1.0 kb Hind III fragment of pBHL-15 containing the FlgG gene produced clone pB5X6. The flgF gene was identified directly upstream of the flqG gene in the clone. The flgF gene was identified directly upstream of the flgG gene in the clone. The flgFG operon was sequenced in both orientations (FIG. 1). No flagellar related genes were detected in the flanking regions of the flgFG operon.

This fact indicates that the flagellar structural genes of *C. jejuni* are organized differently from other bacteria, since all the flgFG operons that have been isolated to date are located within a larger cluster of other flagella structural genes (Refs. 5, 6, 14 and 27).

The purified and isolated DNA molecules comprising at least a portion coding for a basal body rod protein of a species of Campylobacter typified by the embodiments described herein are advantageous as:

nucleic acid probes for the specific identification of Campylobacter strains in vitro or in vivo.

the products encoded by the DNA molecules are useful as diagnostic reagents, antigens for the production of Campylobacter-specific antisera, for vaccination against the diseases caused by species of Campylobacter and (for example) detecting infection by Campylobacter.

peptides corresponding to portions of the basal body rod protein as typified by the embodiments described herein are advantageous as diagnostic reagents, antigens for the production of Campylobacter-specific antisera, for vaccination against the diseases caused by species of Campylobacter and (for example) for detecting infection by Campylobacter.

The basal body rod protein encoded by the nucleic acid molecules of the present invention, fragments and analogs thereof, and peptides containing sequences corresponding to portions of the basal body rod protein that are conserved between various isolates of Campylobacter and other bacteria that produce basal body rod protein, are useful in diagnosis of and immunization against diseases caused by any bacterial strain that produces basal body rod protein. In particular, peptides containing the sequences conserved in the basal body rod protein proteins of many bacterial pathogens that produce basal body rod protein and are appropriate for diagnosis of and immunization against diseases caused by bacteria that produce basal body rod protein.

It is clearly apparent to one skilled in the art, that the various embodiments of the present invention have many applications in the fields of vaccination, diagnosis, treatment of, for example, Campylobacter infections, and infections with other bacterial pathogens that produce basal body rod protein and the generation of immunological reagents. A further non-limiting discussion of such uses is further presented below.

1. Vaccine Preparation and Use

Immunogenic compositions, suitable to be used as vaccines, may be prepared from basal body rod proteins, analogs and fragments thereof, peptides and nucleic acid molecules encoding such basal body proteins, fragments and analogs thereof and peptides as disclosed herein. The vaccine elicits an immune response which produces antibodies, including anti-basal body rod protein antibodies and antibodies that are eopsonizing or bactericidal. Should the vaccinated subject be challenged by Campylobacter or other bacteria that produce a basal body rod protein, the antibodies bind to the basal body rod protein and thereby inactivate the bacteria. Opsonizing or bactericidal antibodies may be particularly useful for providing protection.

Vaccines containing peptides are generally well known in the art, as exemplified by U.S. Pat. Nos. 4,601,903; 4,599,231; 4,599,230; and 4,596,792; all of which references are incorporated herein by reference. Immunogenic compositions including vaccines may be prepared as injectables, as liquid solutions or emulsions. The nucleic acid molecules, basal body rod proteins, analogs and fragments thereof and/or peptides may be mixed with pharmaceutically acceptable excipients which are compatible with the basal body rod protein, fragments analogs or peptides. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the nucleic acid molecule, basal body rod protein, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the basal body rod protein, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

Thus, the nucleic acid molecules encoding the basal body rod proteins, fragments or analogs thereof, of the present invention may also be used directly for immunization by administration of the nucleic acid molecule (including DNA molecules) directly, for example by injection for genetic immunization or by constructing a live vector such as Salmonella, BCG, adenovirus, poxvirus, vaccinia or poliovirus. A discussion of some live vectors that have been used to carry heterologous antigens to the immune system are discussed in for example O'Hagan (Ref 15). Processes for the direct injection of DNA into test subjects for genetic immunization are described in, for example, Ulmer et al. (Ref. 16).

The use of peptides in vivo may first require their chemical modification since the peptides themselves may not have a sufficiently long serum and/or tissue half-life and/or sufficient immunogenicity. Such chemically modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

Examples of side chain modifications contemplated by the present invention include modification of amino groups such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2, 3-butanedione, phenylglyoxal and glyoxal.

The carboxyl group may be modified by carbodimide activation via o-acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butylglycine, norvaline, phenylglycine, ornithine, sarcosine, 4-amino-3-hydroxy-6-methylheptanoic acid, 2-thienyl alanine and/or D-isomers of amino acids.

Immunogenicity can be significantly improved if the antigens are co-administered with adjuvants, commonly used as an 0.05 to 1.0 percent solution in phosphate-buffered buffered saline. Adjuvants enhance the immunogenicity of an antigen but are not necessarily immunogenic themselves.

Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminim phosphate (collectively commonly referred to as alum) are routinely used as adjuvants in human and veterinary vaccines. The efficacy of alum in increasing antibody responses to diptheria and tetanus toxoids is will established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes ISCOMs), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (Ref. 17), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Weismuller (Ref. 18), describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. (Ref. 19), reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-s-[2,3-bis(palmitylxy)-(2RS)-propyl-[R]-cysteine (TPC).

2. Immunoassays

The basal body rod protein, analogs and fragments thereof and/or peptides of the present invention are useful as immunogens, as antigens in immunoassays including enzyme-linked immunosorbent assays (ELISA), RIAs and other non-enzyme linked antibody binding assays or procedures known in the art for the detection of anti-bacterial, Campylobacter, basal body rod protein and/or peptide antibodies. In ELISA assays, the basal body rod proteins, analogs, fragments and/or peptides corresponding to portions of basal body rod protein are immobilized onto a selected surface, for example a surface capable of binding proteins or peptides such as the wells of a polystyrene microtiter plate. After washing to remove incompletely adsorbed basal body rod protein, analogs, fragments and/or peptides, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface. The selected peptides may be from the conserved regions of basal to enhance the cross-species detection unless one particular bacterial species is to be detected. In that event, a polypeptide is selected which is unique to the basal body protein of that particular species. Normally, the peptides are in the range of 12 residues and up and preferably 14 to 30 residues. It is understood however, that a mixture of peptides may be used either as an immunogen in a vaccine or as a diagnostic agent. There may be circumstances where a mixture of peptides from the conserved regions and/or from the non-conserved regions are used to provide cross-species protection and/or specific diagnosis. In this instance, the mixture of peptide immunogens is commonly referred to as a "cocktail" preparation for use as a vaccine or diagnostic agent.

The immobilizing surface is then contacted with a sample such as clinical or biological materials to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from 2 to 4 hours, at temperatures such as of the order of 25° to 37 C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound basal body rod protein, analogs, fragments and/or peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a visible spectra spectrophotometer.

3. Use of Sequences as Hybridization Probes

The nucleotide sequences of the present invention, comprising the sequence of the basal body rod protein, fragments or analogs thereof, now allow for the identification and cloning of the basal body rod protein genes from any species of Campylobacter and other bacteria that have basal body rod protein genes.

The nucleotide sequences comprising the sequence of the basal body rod protein genes of the present invention are useful for their ability to selectively form duplex molecules with complementary stretches of other basal body rod protein genes. Depending on the application, a variety of hybridization conditions may be employed to achieve varying degrees of selectivity of the probe toward the other basal body rod protein genes. For a high degree of selectivity, relatively stringent conditions are used to form the duplexes, such as low salt and/or high temperature conditions, such as provided by 0.02M to 0.15M NaCl at temperatures of between about 50 C. to 70 C. For some applications, less stringent hybridization conditions are required such as 0.15M to 0.9M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the basal body rod protein genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing TfR gene sequences.

The nucleic acid sequences of basal body rod protein genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids or even tissues, is adsorbed or otherwise affixed to a selected matrix or surface. The fixed, single-stranded nucleic acid is then subjected to specific hybridization with selected probes comprising the nucleic acid sequences of the basal body rod protein genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. As with the selection of peptides, it is preferred to select nucleic acid sequence portions which are conserved among species of bacteria (including Campylobacter) that produce basal body proteins, such as nucleic acid sequences encoding the conserved sequences of FIG. 2. The selected probe may be at least 18 bp and may be in the range of 30 bp to 90 bp long.

4. Expression of the Basal Body Rod Protein Genes

Plasmid vectors containing replicon and control sequences which are derived from species compatible with the host cell may be used for the expression of the basal body rod protein genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. Coli* LE392.

Promoters commonly used in recombinant DNA construction include the β-lactamase (penicillinase) and lactose promoter systems (Refs 20, 21, 22) and other microbial promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the basal body rod protein genes, fragments, analogs or variants thereof include *E. coli*, Bacillus species, Campylobacter, fungi, yeast or the baculovirus expression system may be used.

In accordance with this invention, it is preferred to make the protein by recombinant methods, particularly when the naturally occurring basal body rod protein as purified from a culture of a species of Campylobacter may include trace amounts of toxic materials or other contaminants. This problem can be avoided by using recombinantly produced basal body rod protein in heterologous systems which can be isolated from the host in a manner to minimize contaminants in the purified material. Particularly desirable hosts for expression in this regard include Gram positive bacteria which do not have LPS and are therefore endotoxin free. Such hosts include species of Bacillus and may be particularly useful for the production of non-pyrogenic basal body rod proteins, fragments or analogs thereof. Furthermore, recombinant methods of production permit the manufacture of FlgF or FlgG or fragments thereof separate from one another which is distinct from the normal combined proteins present in Campylobacter.

As noted above, bacteria that lack functional flagella and are substantially reduced in motility are also reduced in virulence. The nucleic acid molecules encoding basal body proteins of flagella as provided herein allow for the specific modification of flagella (by, for example, site-specific mutagenesis of the genes encoding the basal body proteins) to functionally disable the flagella. Bacteria having such functionally disabled flagella will be rendered substantially non-motile and substantially avirulent. Such avirulent (or attenuated) bacteria are useful as immunogens for vaccination against disease caused by Campylobacter or other bacteria that produced flagella containing basal body rod proteins as encoded by genes of the present invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used but not explicitly described in this disclosure and these Examples are amply reported in the scientific literature and are well within the ability of those skilled in the art.

Example 1

This Example describes the analysis of a clone encoding the basal body rod protein of the flagella of *Campylobacter jejuni.*

Plasmid pBSXS6 (FIG. 3) contains the flgFG operon of *C. jejuni*. The flgFG operon was sequenced in both orientations (Ref 24) and the determined nucleic acid sequence (SEQ ID No: 1) is shown in FIG. 1.

A 20-mer oligonucleotide, F1, 5'-GTTACCATTCCGCCAGTTGC-3' (SEQ ID No: 11) located at nt 123 to nt 142 (FIG. 1), is complementary to the mRNA transcript of the flgF gene and was used to locate the transcriptional start point of this gene. Two transcription start points were detected at nt 86 and nt 55 in *E. coli* containing plasmid pBSXS6. No transcriptional start site in *C. jejuni* RNA was detected. This may have been due to the low level of the flgFG mRNA transcript in the *C. jejuni* RNA. Another oligonucleotide complementary to flgG mRNA transcript was used for primer extension, but was unsuccessful in locating the transcriptional start site of flgG. A single mRNA transcript was seen in the in vitro transcription of pBSd43, a deletion clone of pBSXS6 containing the complete sequence of flgf and flgG but not the upstream sequence of flgF. Also, since the flgG encoding sequence is located only 28 nucleotides downstream of the stop codon of flgF, the two genes may exist as a single mRNA transcript. The organization of flgF and flgG genes as an operon has been observed in many other bacteria (Ref. 6, 14, 27).

The flgF gene (SEQ ID No: 2) is an 810-nt sequence encoding a 270 amino acid protein (SEQ ID No: 4) (FIG. 1). The deduced molecular weight of this protein (FlgF) is 30.2 kD. Five nucleotides preceding the Met start codon of the flgF gene at nucleotides 91 to nt 96, is 5'-AGGTGA-3', which matches four of the six nucleotides of a typical Shine-Dalgarno sequence (Ref. 25) (FIG. 1). At nt 41 to 46, a sequence TAAAAG conserved in four of the six nucleotides of the Pribnow box (TATAAT) was seen. Upstream of this putative-10 region at nucleotides 15–20 is TTCAAA which matches the -35 concensus sequence (TTGACA) in four of the six nucleotides (Ref. 26). Both these -35 and -10 regions are homologous to the consensus sequences of the class I promoter commonly found for housekeeping genes. However, the transcriptional start site at nt 86 appears to utilize a class II promoter of the flagellar genes (Ref. 2) with the putative−10 sequence at nucleotide 69–76, AGTTATAA. This promoter region is more likely to be the one used by *C jejuni* since other studies indicate that the flagellar structural protein genes tend to use the class I operon system (Ref. 2) that is mediated by a flagellum-specific sigma factor instead of the one for housekeeping genes. The stop codon for the flgF gene is located at nucleotide 911 and the flgG gene (SEQ ID No: 3) begins 28 basepairs downstream. The 789-nt sequence of the flgG gene (SEQ ID No: 3) along with the predicted 263 amino acids of the FlgG protein (SEQ ID No: 5) are shown in FIG. 1. The molecular weight of the flgG protein is 27.7 kD. Five nucleotides upstream of the flgG start codon is another possible Shine-Delgarno sequence at nt 932 to nucleotides 935, 5' -AGGA-3' (FIG. 1).

Example 2

This Example describes a comparative analysis of the FlgF and FlgG proteins.

The predicted amino acid sequence of the *C jenuni* FlgF protein is approximately 30% homologous to the amino acid sequence of *Campylobacter crescentus* and *Salmonella typhimurium* FlgF. The alignment of the three FlgF protein sequence indicates two areas of extensive homology (FIG. 2). The FlgG proteins were more conserved between the different bacteria; homologies were in the range of 40% to 47%. Similarly, the FlgF and FlgG proteins of *C. jejuni* also share an extensive homology among themselves. At the N-terminal end of the FlgF and FlgG proteins, a conserved sequence of NNLAN (SEQ ID No: 12) (FIG. 2) was present which has also been seen in most other hook and rod proteins studied. This particular region has been suggested as a possible recognition site of the transport of the structural protein of cellular surface or as a structural motif for the arrangement of the hook and rod proteins. At the carboxyl end of the protein, conserved sequence (FIG. 2) are likely to be structural motifs for the assembly of the flagellum.

Example 3

This Example illustrates the expression of the *C. jejuni* flgF and flgG genes in *E. coli.*

Clones containing the flgFG operon were subcloned into either pUCl9 or pBluescript vectors (FIG. 3). pBSXS6 is a pBluescript recombinant containing the 4.8 kb SalI-XbaI *C.*

Figure 4:
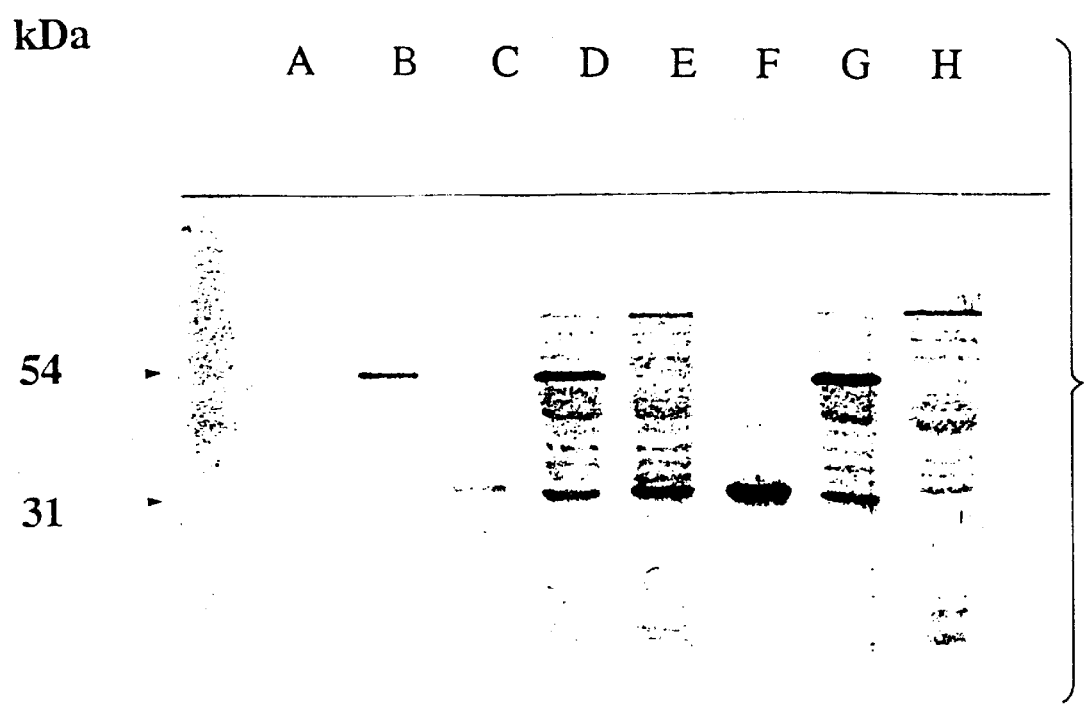
FIG. 4 contains a Maxicell Analysis. Various plasmids were transformed into *E. coli* strain DR1984 for plasmid encoded protein analysis (ref. 35). Lanes: (a) pUC19; (b) pUH4; (c) pBluescript; (d) pBSXS6; (e) pBS10r; (f)pBS10r; (g) pBSd43; and (h) no plasmid. The arrows and the number indicated location and size of the protein products in kD.

*jejuni* insert. pUH4, a pUC19 recombinant contains the 4.5 kb EcoRI fragment of pBSXS6. pBSd43, is a deletion clone of pBSXS6 with the upstream region of flgF removed. pBS10 and pBS10r are pBluescript recombinants constructed with the 1.0 kb HindIII fragment of pBSXS6 containing only the incomplete flgF gene in forward and reverse orientations respectively. These recombinants along with pBluescript and pUC19 were transformed into *E. coli* strain DR1984 (Ref. 28) to identify plasmid encoded proteins. The preparation of the plasmid encoded proteins is described in Chan and Bibgham (Ref. 11). The UV-irradiated cells were labelled with [$^{35}$S] methionine, lysed and the protein extracts electrophoresed on a 12% SDS-polyacrylamide gel containing 0.1% SDS and a 5% stacking gel. The gel was electrophesed at 120 volts for 1.5 hours, stained with Coomassie brilliant blue R-50 for 30 minutes, destained overnight in 10% glacial acetic acid and 30% methanol. The gel was impregnated with EN$^3$HANCE for 1 hour, washed with H$_2$O and then dried on the gel dryer for 2 hours at 70° C. The gel was the exposed to Kodak XAR-5 film for 3 hours. In FIG. 4, the 31 kD protein is a beta-lactamase, but in pBS10 and pBS10r the 31 kD bands were more intense suggesting also the presence of the incomplete FlgF protein product with the addition of 12 amino acids from the vector sequence. The pBS10r clone has a more pronounced 31 kD band due to the orientation of the insert which allowed the usage of both its own and the vectors' lac promoter (FIG. 3). The 54 kDA protein seen in pUH4, pBSXS6, and pBSd43 may be the flgFG fusion protein since pBSd43 which does not contain any upstream sequence of flgFG, and the downstream sequence is not capable of producing a protein of this size. The presence of a single translated flgF and flgG protein may be due to ribosomal frameshifting. The phenomenum of ribosomal frameshifting has been documented in both prokaryotic and eukaryotic cells (Refs 29, 30, 31). Currently, three types of frameshiftings have been described. The (+1) also known as rightward ribosomal frameshift has been observed in *Escherichia coli* trpR and polypeptide release factor 2 (pRFB) (Refs 29, 30). Similarly the leftward (−1) frameshift has been observed in the gag-pol fusion protein of HIV-1 (Ref. 32). The last type of frameshift involves the deletion of a region of RNA due to the formation of loop structure (Refs 33, 34).

SUMMARY OF THE DISCLOSURE

In summary of this disclosure, the flgFG operon of *Campylobacter jejuni* has been cloned and sequenced. Although the FlgF and FlgG proteins exhibit homology of other bacterial FlgF and FlgG proteins, the structural organization of *C. jejuni* flagellar genes exhibits variations from other bacteria, since no other flagellar related protein genes have been identified immediately upstream of the flgFG operon in *C. jejuni*. Modifications are possible within the scope of this invention.

LIST OF REFERENCES

1. Penner J. L., (1988) Clin. Microbiol. Rev. 1: 157.
2. Macnab, Robert M. (1992) Annu. Rev. Genet. 26: 131.
3. Aizawa, S. et al., J. Bact. 161 (1985) 836.
4. Komeda, Y. et al., J. Bacteriol. 134: (1978) 655.
5. Homma M. et al., J. Bacteriol. 169: (1987) 3617.
6. Homma M. et al., J. Mol. Biol. 211: (1987) 465.
7. Kazuhiro et al., J. Bacteriol. 176: (1994) 3598
8. Nuijten, P. J. M. et al, J. Biol. Chem. 256: (1990) 17798.
9. Fisher S. H. and Nachamkim, I., (1991) Mol. Microbiol. 5: 1151–1158.
10. Khawaja, R. et al., Current Microbiol. 24: (1992) 213.
11. Chan, V. L. et al., Gene 73: (1988), 185.
12. Homma M. et al., J. Mol. Biol. 213: (1990) 819.
13. Albertini. A. M. et al., J. Bacteriol. 173 (1991) 3573.
14. Dingwall. A. et al., J. Mol. Biol. 228: (1992) 1147.
15. O'Hagan (1992) Clin Pharmokinet. 22:1.
16. Ulmer et al., (1993) Curr. Opinion Invest. Drugs. 2(9): 983–989.
17. Nixon-George et al., (1990) J. Immunol. 14:4798.
18. Weismuller et al., (1989) Vaccine 8:29.
19. Deres et al., (1989) Nature 342:651.
20. Chang et al., (1978) Nature 375:615.
21. Itakura et al., (1977) Science 198:1056.
22. Goeddel et al., (1979) Nature 281:544.
23. Goeddel et al., (1980) Nucl. Acids Res. 8:4057
24. Henikoff, S., Gene 28: (1984) 351.
25. Gold, L., Annu. Rev. Biochem. 57: (1988) 199.
26. Hawley, D. K. et al., Nucl. Acid Res. 11: (1983) 2237.
27. Zuberi, A. R., J. Bacteriol. 173: (1991) 710.
28. Davis. B. D. et al., J. Bacteriol. 60: (1950) 17.
29. Benhar, et al. Mol. Microbiol. 6: 2777.
30. Curran, J. F., Nucl. Acid. Res. 21: (1983) 1837.
31. Clare, J. J. et al., Proc. Natl. Acad. Sci. 85: (1988) 6816.
32. Yelverton, E. et al., Microbiol. 11: (1994) 303.
33. Brierley, I. et al., Cell 57: (1989) 537.
34. Chandler, M. et al., Mol. Microbiol. 7: (1983) 497.
35. Sancer, B. et al., J. Bacteriol. 137: (1979) 692.

What we claim is:

1. A purified and isolated nucleic acid molecule having a nucleotide sequence selected from the group consisting of:
   (a) the entire sequence set out in FIG. 1 (SEQ ID No: 1), the sequence of the flgF gene (SEQ ID No: 2), the sequence of the flgG gene (SEQ ID No: 3) or the full length complementary sequence of any one of said sequences;
   (b) a nucleotide sequence encoding the amino acid sequence of the FlgF protein (SEQ ID No: 4), a sequence encoding the FlgG protein (SEQ ID No: 5) or the full length complementary sequence thereto; and
   (c) a nucleotide sequence encoding a functional FlgF basal body rod protein of a flagellum of a strain of Campylobacter which has at least about 90% nucleotide sequence identity with any one of the nucleotide sequences defining FlgF in (a) or (b).

2. A vector adapted for transformation of a host comprising the nucleic acid molecule of claim 1.

3. The vector of claim 2 having the identifying characteristics of plasmid pBSXS6, pUH4 or pBSd43.

4. An expression vector adapted for transformation of a host comprising the nucleic acid molecule of claim 1 and expression means operatively coupled to the nucleic acid molecule for expression by the host of said basal body rod protein of a strain of Campylobacter.

5. The expression vector of claim 4, wherein the nucleic acid molecule encodes both the FlgF and FlgG proteins of the Campylobacter strain.

6. The expression vector of claim 4, wherein the nucleic acid molecule encodes only the FlgF or only the FlgG protein of the Campylobacter strain.

7. The expression vector of claim 4, wherein the expression means includes a nucleic acid portion encoding a leader sequence for secretion from the host of the basal body rod protein.

8. The expression vector of claim 4, wherein the expression means includes a nucleic acid portion encoding a lipidation signal for expression from the host of a lipidated form of the basal body rod protein.

9. A transformed host containing an expression vector as claimed in claim 4.

10. A live vector for delivery of basal body rod protein to a host, comprising a vector containing the nucleic acid molecule of claim 1.

11. The live vector of claim 10, wherein the vector is selected from the group consisting of Salmonella, BCG, adenovirus, poxvirus, vaccinia and poliovirus.

12. A diagnostic kit for determining the presence of nucleic acid encoding the basal body rod protein of a strain of Campylobacter in a sample, comprising:
   (a) the nucleic acid molecule of claims 1;
   (b) a reagent for contacting the nucleic acid with the sample to produce duplexes comprising the nucleic acid molecule and any said nucleic acid present in the sample and hybridizable with the nucleic acid molecule; and
   (c) indicator for determining production of the duplexes.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1800 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: join(101..910, 942..1730)

( x i ) SEQUENCE DESCRIPTION: SEQ ID NO:1:

```
TCTCCTAATA ATCTTTCAAA TATTTATTTT TCTTTGTTTT TAAAAGTTGG AACACTCTTT         60

GCTTTTATAG TTATAAAATC TTAAATTTAT AGGTGAAAAT ATG CAA AAT GGA TAT         115
                                             Met Gln Asn Gly Tyr
                                              1               5

TAT CAA GCA ACT GGC GGA ATG GTA ACT CAG TTT AAT AAA CTT GAT GTG         163
Tyr Gln Ala Thr Gly Gly Met Val Thr Gln Phe Asn Lys Leu Asp Val
            10              15                          20

ATT ACT AAT AAT CTT GCC AAT ATC AAT ACA AGT GGA TAT AAA AGA GAT         211
Ile Thr Asn Asn Leu Ala Asn Ile Asn Thr Ser Gly Tyr Lys Arg Asp
        25              30                          35

GAT GTG GTT ATT GCA GAT TTT AAA AGG ATT TTT AAA GAA ACT CAG GAT         259
Asp Val Val Ile Ala Asp Phe Lys Arg Ile Phe Lys Glu Thr Gln Asp
    40              45                          50

GAG TTG CCT ATA GAA AAT CAC ACA AGA GAT GCA TCT CGT TTT GTA AAT         307
Glu Leu Pro Ile Glu Asn His Thr Arg Asp Ala Ser Arg Phe Val Asn
    55              60                          65

ACT ACA ATA GAT GGA ATC CCA CAA GTT TCT CAA GAA TAT ACG GAT TTT         355
Thr Thr Ile Asp Gly Ile Pro Gln Val Ser Gln Glu Tyr Thr Asp Phe
70              75                          80                  85

AGC CTA GGT TCT TTA AAG GCC ACA AAC AAT CCT TTG GAT TTG GCA ATG         403
Ser Leu Gly Ser Leu Lys Ala Thr Asn Asn Pro Leu Asp Leu Ala Met
            90              95                          100

ACT AGA GAA GAT GCT TTT TAT TTG GTT CAG ACC AAA GAT GGA GAA GTA         451
Thr Arg Glu Asp Ala Phe Tyr Leu Val Gln Thr Lys Asp Gly Glu Val
            105             110                         115

AGA TTA ACC AAA GAT GGA AAT TTT CAA CTT GAT GAT GAG GGT TAT TTG         499
Arg Leu Thr Lys Asp Gly Asn Phe Gln Leu Asp Asp Glu Gly Tyr Leu
            120             125                         130

GTA AAT AAG CAA GGA TAC AAG GTA TTA AGT AGT GAT TAT TTT AAT AAT         547
Val Asn Lys Gln Gly Tyr Lys Val Leu Ser Ser Asp Tyr Phe Asn Asn
    135             140                         145

CCT CAG AAT GCT GGC ATA CGC ATT CCT AAT AGT GCT GTT CAA ATT AGC         595
Pro Gln Asn Ala Gly Ile Arg Ile Pro Asn Ser Ala Val Gln Ile Ser
150             155                         160                 165

GTT GAT AAA AAC GGA AGC ATT GAA GTT GAT GGA GCT CAA AAT GCA AGA         643
Val Asp Lys Asn Gly Ser Ile Glu Val Asp Gly Ala Gln Asn Ala Arg
            170             175                         180

TTA TTT GTA GCA CAA GTA GAT GAT ATA AGA GCT TTG CAA AAA GAT GGG         691
Leu Phe Val Ala Gln Val Asp Asp Ile Arg Ala Leu Gln Lys Asp Gly
            185             190                         195

GAT AAT GTC TAT AAA ATA GAT GAT CTA ACC CGT ATT AGA GAT TTG AAA         739
Asp Asn Val Tyr Lys Ile Asp Asp Leu Thr Arg Ile Arg Asp Leu Lys
            200             205                         210

AAC TCC AAT GCT ATT CGC CAA GGT TTT TCT CAG GGA TCA AAT GTT AAT         787
Asn Ser Asn Ala Ile Arg Gln Gly Phe Ser Gln Gly Ser Asn Val Asn
            215             220                         225

CCA GTT ACT GAA ATG GTA GGA CTG ATT GAA GCA AAC AGA ATG GTA GAA         835
Pro Val Thr Glu Met Val Gly Leu Ile Glu Ala Asn Arg Met Val Glu
230             235                         240                 245

ATG TAT CAA AAA GTT ATG ACA GCT CAT ATG GAT GAC TTA AAT CAA GAA         883
Met Tyr Gln Lys Val Met Thr Ala His Met Asp Asp Leu Asn Gln Glu
            250             255                         260

GCT ATC AAT AAG CTT GCA GCT GTT AAA TAATTTAAAA TAAATAAAA                930
Ala Ile Asn Lys Leu Ala Ala Val Lys
            265             270
```

```
AAGGATTAAA A ATG ATG AGA TCA CTT CAT ACT GCT GCT ACA GGA ATG GTA         980
              Met Met Arg Ser Leu His Thr Ala Ala Thr Gly Met Val
                              275                 280

GCG CAG CAA ACA CAA ATT GAT GTT ACT TCA AAT AAC ATC GCC AAT GTT         1028
Ala Gln Gln Thr Gln Ile Asp Val Thr Ser Asn Asn Ile Ala Asn Val
285                 290                 295

AAT ACA GCA GGT TTT AAG AAA AGT CGC GCA GAA TTT GCT GAT CTT ATG         1076
Asn Thr Ala Gly Phe Lys Lys Ser Arg Ala Glu Phe Ala Asp Leu Met
300                 305                 310                 315

TAT CAA GTT ATG AAG TAT GCA GGA ACT TCA ACT TCA GCT ACT ACT CTT         1124
Tyr Gln Val Met Lys Tyr Ala Gly Thr Ser Thr Ser Ala Thr Thr Leu
                320                 325                 330

TCT CCT TCG GGT ATA GAA GTG GGT GTG GGT GTG CGT CCA ACA GCG GTA         1172
Ser Pro Ser Gly Ile Glu Val Gly Val Gly Val Arg Pro Thr Ala Val
            335                 340                 345

ACT AAA GTT TTT ACT GAA GGA AAT TTA AAA TCA ACA AGT ACT GAT GGT         1220
Thr Lys Val Phe Thr Glu Gly Asn Leu Lys Ser Thr Ser Thr Asp Gly
        350                 355                 360

CTT GAT ATG GCT ATT GCA GGT AAT GGG TTT TTT CAA ATA CAA CTT CCT         1268
Leu Asp Met Ala Ile Ala Gly Asn Gly Phe Phe Gln Ile Gln Leu Pro
365                 370                 375

GAT GGC ACT ATA GAA ATG GGC AAT TTA CAA AAG ATA ATG AAG GAT AAT         1316
Asp Gly Thr Ile Glu Met Gly Asn Leu Gln Lys Ile Met Lys Asp Asn
380                 385                 390                 395

GAA GGT AAT ATT GTA AAT TCA GAT GGT TAT AGA CTT TTA CCT GAA ATG         1364
Glu Gly Asn Ile Val Asn Ser Asp Gly Tyr Arg Leu Leu Pro Glu Met
                400                 405                 410

ACA ATA CCT GAA GGC GCA ACA GCA ATT AAT GTT GCT ACA GAT GGA ACC         1412
Thr Ile Pro Glu Gly Ala Thr Ala Ile Asn Val Ala Thr Asp Gly Thr
            415                 420                 425

GTT TCT GTA ATG CTA CCA GGG GAG CAA CAA GAA ACT CAA ATT GGC CAA         1460
Val Ser Val Met Leu Pro Gly Glu Gln Gln Glu Thr Gln Ile Gly Gln
        430                 435                 440

GTG GAG CTA GTT CAG TTT ATA AAT CCA GCG GGT CTT CAT TCT ATG GGT         1508
Val Glu Leu Val Gln Phe Ile Asn Pro Ala Gly Leu His Ser Met Gly
445                 450                 455

GAT AAT CTT TAT CTT GAA ACA GGA GCA AGT GGT GCA CCT GTT GCG GGT         1556
Asp Asn Leu Tyr Leu Glu Thr Gly Ala Ser Gly Ala Pro Val Ala Gly
460                 465                 470                 475

ATA GCA GGA CAA GAT GGG CTT GGA ACA ATA AGA CAT GGA TTT ATA GAA         1604
Ile Ala Gly Gln Asp Gly Leu Gly Thr Ile Arg His Gly Phe Ile Glu
                480                 485                 490

CTT AGT AAT GTT CAG CTT GTT GAA GAA ATG ACA GAT CTT ATC ACA GGA         1652
Leu Ser Asn Val Gln Leu Val Glu Glu Met Thr Asp Leu Ile Thr Gly
            495                 500                 505

CAA AGA GCT TAT GAA GCG GGT TCT AAG GCC ATT ACA ACA AGT GAT GAT         1700
Gln Arg Ala Tyr Glu Ala Gly Ser Lys Ala Ile Thr Thr Ser Asp Asp
        510                 515                 520

ATG CTA GGA ATT GTA AAT CAG CTT AAG CGA TAGTTGATAT AAAATAAATA           1750
Met Leu Gly Ile Val Asn Gln Leu Lys Arg
            525                 530

ATTTTTAATT CTTTTTTGTT TAATGGCGTG TTAAACGCCA TTAAATTTTT                  1800
```

( 2 ) INFORMATION FOR SEQ ID NO:2:

( i ) SEQUENCE CHARACTERISTICS:
        ( A ) LENGTH: 810 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ATGCAAAATG GATATTATCA AGCAACTGGC GGAATGGTAA CTCAGTTTAA TAAACTTGAT        60
GTGATTACTA ATAATCTTGC CAATATCAAT ACAAGTGGAT ATAAAAGAGA TGATGTGGTT       120
ATTGCAGATT TTAAAAGGAT TTTTAAAGAA ACTCAGGATG AGTTGCCTAT AGAAAATCAC       180
ACAAGAGATG CATCTCGTTT TGTAAATACT ACAATAGATG GAATCCCACA AGTTTCTCAA       240
GAATATACGG ATTTTAGCCT AGGTTCTTTA AAGGCCACAA ACAATCCTTT GGATTTGGCA       300
ATGACTAGAG AAGATGCTTT TTATTTGGTT CAGACCAAAG ATGGAGAAGT AAGATTAACC       360
AAAGATGGAA ATTTTCAACT TGATGATGAG GGTTATTTGG TAAATAAGCA AGGATACAAG       420
GTATTAAGTA GTGATTATTT TAATAATCCT CAGAATGCTG GCATACGCAT TCCTAATAGT       480
GCTGTTCAAA TTAGCGTTGA TAAAAACGGA AGCATTGAAG TTGATGGAGC TCAAAATGCA       540
AGATTATTTG TAGCACAAGT AGATGATATA AGAGCTTTGC AAAAAGATGG GGATAATGTC       600
TATAAAATAG ATGATCTAAC CCGTATTAGA GATTTGAAAA ACTCCAATGC TATTCGCCAA       660
GGTTTTTCTC AGGGATCAAA TGTTAATCCA GTTACTGAAA TGGTAGGACT GATTGAAGCA       720
AACAGAATGG TAGAAATGTA TCAAAAAGTT ATGACAGCTC ATATGGATGA CTTAAATCAA       780
GAAGCTATCA ATAAGCTTGC AGCTGTTAAA                                        810
```

( 2 ) INFORMATION FOR SEQ ID NO:3:

( i ) SEQUENCE CHARACTERISTICS:
( A ) LENGTH: 270 amino acids
( B ) TYPE: amino acid
( C ) STRANDEDNESS: single
( D ) TOPOLOGY: linear ( x i ) SEQUENCE DESCRIPTION: SEQ ID NO:3:

```
Met Gln Asn Gly Tyr Tyr Gln Ala Thr Gly Gly Met Val Thr Gln Phe
 1               5                  10                  15

Asn Lys Leu Asp Val Ile Thr Asn Asn Leu Ala Asn Ile Asn Thr Ser
                 20                  25                  30

Gly Tyr Lys Arg Asp Asp Val Val Ile Ala Asp Phe Lys Arg Ile Phe
             35                  40                  45

Lys Glu Thr Gln Asp Glu Leu Pro Ile Glu Asn His Thr Arg Asp Ala
     50                  55                  60

Ser Arg Phe Val Asn Thr Thr Ile Asp Gly Ile Pro Gln Val Ser Gln
 65                  70                  75                  80

Glu Tyr Thr Asp Phe Ser Leu Gly Ser Leu Lys Ala Thr Asn Asn Pro
                 85                  90                  95

Leu Asp Leu Ala Met Thr Arg Glu Asp Ala Phe Tyr Leu Val Gln Thr
            100                 105                 110

Lys Asp Gly Glu Val Arg Leu Thr Lys Asp Gly Asn Phe Gln Leu Asp
        115                 120                 125

Asp Glu Gly Tyr Leu Val Asn Lys Gln Gly Tyr Lys Val Leu Ser Ser
    130                 135                 140

Asp Tyr Phe Asn Asn Pro Gln Asn Ala Gly Ile Arg Ile Pro Asn Ser
145                 150                 155                 160

Ala Val Gln Ile Ser Val Asp Lys Asn Gly Ser Ile Glu Val Asp Gly
                165                 170                 175

Ala Gln Asn Ala Arg Leu Phe Val Ala Gln Val Asp Asp Ile Arg Ala
            180                 185                 190

Leu Gln Lys Asp Gly Asp Asn Val Tyr Lys Ile Asp Asp Leu Thr Arg
        195                 200                 205
```

```
        Ile  Arg  Asp  Leu  Lys  Asn  Ser  Asn  Ala  Ile  Arg  Gln  Gly  Phe  Ser  Gln
             210                      215                      220

Gly  Ser  Asn  Val  Asn  Pro  Val  Thr  Glu  Met  Val  Gly  Leu  Ile  Glu  Ala
        225                      230                      235                      240

Asn  Arg  Met  Val  Glu  Met  Tyr  Gln  Lys  Val  Met  Thr  Ala  His  Met  Asp
                            245                      250                      255

Asp  Leu  Asn  Gln  Glu  Ala  Ile  Asn  Lys  Leu  Ala  Ala  Val  Lys
                       260                      265                      270
```

( 2 ) INFORMATION FOR SEQ ID NO:4:

( i ) SEQUENCE CHARACTERISTICS:
        ( A ) LENGTH: 789 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
ATGATGAGAT  CACTTCATAC  TGCTGCTACA  GGAATGGTAG  CGCAGCAAAC  ACAAATTGAT    60
GTTACTTCAA  ATAACATCGC  CAATGTTAAT  ACAGCAGGTT  TTAAGAAAAG  TCGCGCAGAA   120
TTTGCTGATC  TTATGTATCA  AGTTATGAAG  TATGCAGGAA  CTTCAACTTC  AGCTACTACT   180
CTTTCTCCTT  CGGGTATAGA  AGTGGGTGTG  GGTGTGCGTC  CAACAGCGGT  AACTAAAGTT   240
TTTACTGAAG  GAAATTTAAA  ATCAACAAGT  ACTGATGGTC  TTGATATGGC  TATTGCAGGT   300
AATGGGTTTT  TTCAAATACA  ACTTCCTGAT  GGCACTATAG  AAATGGGCAA  TTTACAAAAG   360
ATAATGAAGG  ATAATGAAGG  TAATATTGTA  AATTCAGATG  GTTATAGACT  TTTACCTGAA   420
ATGACAATAC  CTGAAGGCGC  AACAGCAATT  AATGTTGCTA  CAGATGGAAC  CGTTTCTGTA   480
ATGCTACCAG  GGGAGCAACA  AGAAACTCAA  ATTGGCCAAG  TGGAGCTAGT  TCAGTTTATA   540
AATCCAGCGG  GTCTTCATTC  TATGGGTGAT  AATCTTTATC  TTGAAACAGG  AGCAAGTGGT   600
GCACCTGTTG  CGGGTATAGC  AGGACAAGAT  GGGCTTGGAA  CAATAAGACA  TGGATTTATA   660
GAACTTAGTA  ATGTTCAGCT  TGTTGAAGAA  ATGACAGATC  TTATCACAGG  ACAAAGAGCT   720
TATGAAGCGG  GTTCTAAGGC  CATTACAACA  AGTGATGATA  TGCTAGGAAT  TGTAAATCAG   780
CTTAAGCGA                                                                789
```

( 2 ) INFORMATION FOR SEQ ID NO:5:

( i ) SEQUENCE CHARACTERISTICS:
        ( A ) LENGTH: 263 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
        Met  Met  Arg  Ser  Leu  His  Thr  Ala  Ala  Thr  Gly  Met  Val  Ala  Gln  Gln
        1              5                        10                       15

Thr  Gln  Ile  Asp  Val  Thr  Ser  Asn  Asn  Ile  Ala  Asn  Val  Asn  Thr  Ala
                            20                       25                       30

Gly  Phe  Lys  Lys  Ser  Arg  Ala  Glu  Phe  Ala  Asp  Leu  Met  Tyr  Gln  Val
                       35                       40                       45

Met  Lys  Tyr  Ala  Gly  Thr  Ser  Thr  Ser  Ala  Thr  Thr  Leu  Ser  Pro  Ser
                  50                       55                       60

Gly  Ile  Glu  Val  Gly  Val  Gly  Val  Arg  Pro  Thr  Ala  Val  Thr  Lys  Val
        65                       70                       75                       80

Phe  Thr  Glu  Gly  Asn  Leu  Lys  Ser  Thr  Ser  Thr  Asp  Gly  Leu  Asp  Met
                            85                       90                       95
```

```
        Ala   Ile   Ala   Gly   Asn   Gly   Phe   Phe   Gln   Ile   Gln   Leu   Pro   Asp   Gly   Thr
                          100                             105                             110

Ile   Glu   Met   Gly   Asn   Leu   Gln   Lys   Ile   Met   Lys   Asp   Asn   Glu   Gly   Asn
                          115                             120                             125

Ile   Val   Asn   Ser   Asp   Gly   Tyr   Arg   Leu   Leu   Pro   Glu   Met   Thr   Ile   Pro
                    130                             135                             140

Glu   Gly   Ala   Thr   Ala   Ile   Asn   Val   Ala   Thr   Asp   Gly   Thr   Val   Ser   Val
        145                                 150                             155                             160

Met   Leu   Pro   Gly   Glu   Gln   Gln   Glu   Thr   Gln   Ile   Gly   Gln   Val   Glu   Leu
                                  165                             170                             175

Val   Gln   Phe   Ile   Asn   Pro   Ala   Gly   Leu   His   Ser   Met   Gly   Asp   Asn   Leu
                                180                             185                             190

Tyr   Leu   Glu   Thr   Gly   Ala   Ser   Gly   Ala   Pro   Val   Ala   Gly   Ile   Ala   Gly
                          195                             200                             205

Gln   Asp   Gly   Leu   Gly   Thr   Ile   Arg   His   Gly   Phe   Ile   Glu   Leu   Ser   Asn
                    210                             215                             220

Val   Gln   Leu   Val   Glu   Glu   Met   Thr   Asp   Leu   Ile   Thr   Gly   Gln   Arg   Ala
        225                             230                             235                             240

Tyr   Glu   Ala   Gly   Ser   Lys   Ala   Ile   Thr   Thr   Ser   Asp   Asp   Met   Leu   Gly
                                245                             250                             255

Ile   Val   Asn   Gln   Leu   Lys   Arg
                          260
```

( 2 ) INFORMATION FOR SEQ ID NO:6:

( i ) SEQUENCE CHARACTERISTICS:
        ( A ) LENGTH: 248 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
        Met   Asp   Asn   Ala   Leu   Tyr   Val   Gly   Leu   Ser   Arg   Gln   Met   Thr   Val   Arg
        1                       5                             10                            15

Arg   Glu   Leu   Asp   Ile   Val   Ala   Asn   Ile   Ala   Asn   Ala   Asn   Thr   Thr
                          20                            25                            30

Gly   Phe   Lys   Val   Glu   Asp   Leu   Met   Val   Arg   Thr   Glu   Gln   Ala   Lys   Pro
                    35                            40                            45

Ala   Lys   Thr   Leu   Asp   Gly   Ser   Ser   Pro   Val   Lys   Phe   Val   Met   Asp   Thr
              50                            55                            60

Gly   Val   Arg   Arg   Asn   Phe   Thr   Gln   Gly   Pro   Met   Thr   Lys   Thr   Gly   Gly
        65                            70                            75                            80

Asp   Tyr   Asp   Leu   Ala   Ile   Asn   Gly   Met   Gly   Phe   Phe   Lys   Val   Gln   Ala
                                85                            90                            95

Asn   Gly   Gly   Glu   Arg   Tyr   Thr   Arg   Asp   Gly   Arg   Phe   Thr   Thr   Asn   Pro
                          100                           105                           110

Glu   Gly   Ile   Leu   Val   Thr   Gln   Ala   Gly   Ala   Pro   Val   Leu   Asp   Asp   Gly
                    115                           120                           125

Gly   Gly   Gln   Ile   Thr   Ile   Asp   Pro   Arg   Leu   Gly   Pro   Val   Thr   Val   Gly
                    130                           135                           140

Lys   Asp   Gly   Ile   Val   Ser   Gln   Gly   Ala   Ile   Arg   Val   Ser   Arg   Ile   Gly
        145                           150                           155                           160

Leu   Val   Arg   Pro   Asp   Asp   Leu   Ser   Thr   Phe   Ala   Lys   Asp   Gly   Asp   Asn
                                165                           170                           175

Leu   Tyr   Arg   Asn   Thr   Thr   Asn   Thr   Ala   Pro   Gln   Pro   Val   Thr   Asp   Ala
                          180                           185                           190
```

```
          Gln   Ile   His   Gln   Gly   Met   Leu   Glu   Ala   Ser   Asn   Val   Gln   Pro   Val   Ile
                      195                           200                           205

Glu   Ile   Thr   Lys   Leu   Ile   Glu   Ile   Gln   Arg   Ala   Tyr   Glu   Ser   Val   Ala
                      210                           215                           220

Lys   Met   Met   Asp   Asn   Thr   Ala   Glu   Leu   Ser   Arg   Thr   Pro   Ser   Ser   Val
          225                                 230                           235                           240

Trp   Ala   Arg   Ser   Thr   Arg   Glu   Arg
                                  245
```

(2) INFORMATION FOR SEQ ID NO:7:

(i) SEQUENCE CHARACTERISTICS:
        (A) LENGTH: 262 amino acids
        (B) TYPE: amino acid
        (C) STRANDEDNESS: single
        (D) TOPOLOGY: linear (xi) SEQUENCE DESCRIPTION: SEQ ID NO:7:

```
          Met   Gln   Ala   Leu   Arg   Thr   Ala   Ala   Ser   Gly   Met   Ala   Ala   Gln   Gln   Leu
          1                       5                             10                            15

Asn   Val   Glu   Val   Ile   Ser   Asn   Asn   Ile   Ala   Asn   Met   Asn   Thr   Val   Gly
                            20                            25                            30

Phe   Lys   Arg   Gln   Arg   Ala   Glu   Phe   Gln   Asp   Leu   Leu   Tyr   Gln   Thr   Ile
                      35                            40                            45

Glu   Arg   Ala   Gly   Ser   Gln   Ser   Ser   Ser   Asp   Gly   Asn   Ile   Val   Pro   Thr
                50                            55                            60

Gly   Val   Gln   Val   Gly   Gly   Val   Lys   Ala   Gly   Ser   Val   Tyr   Arg   Ile
          65                            70                            75                            80

Thr   Glu   Gln   Gly   Thr   Pro   Thr   Leu   Thr   Asp   Ser   Pro   Leu   Asp   Leu   Ala
                                  85                            90                            95

Ile   Gln   Gly   Lys   Gly   Tyr   Met   Pro   Ile   Leu   Leu   Pro   Ser   Gly   Glu   Thr
                            100                           105                           110

Ala   Tyr   Thr   Arg   Ala   Gly   Asn   Phe   Ser   Thr   Asn   Asp   Gln   Gly   Gln   Ile
                      115                           120                           125

Val   Thr   Glu   Asp   Gly   Tyr   Leu   Val   Gln   Pro   Gly   Ile   Thr   Ile   Pro   Gln
                130                           135                           140

Asn   Ala   Thr   Asp   Ile   Thr   Ile   Ser   Lys   Ser   Gly   Leu   Val   Gln   Val   Lys
          145                           150                           155                           160

Leu   Asp   Gly   Gln   Pro   Gln   Pro   Gln   Thr   Val   Gly   Gln   Ile   Gln   Leu   Ala
                            165                           170                           175

Asn   Phe   Leu   Asn   Glu   Gly   Gly   Leu   Glu   Ala   Ile   Gly   Asp   Asn   Leu   Phe
                      180                           185                           190

Leu   Glu   Thr   Ala   Ala   Ser   Gly   Ala   Ala   Thr   Leu   Val   Arg   Arg   Ala   Ser
                      195                           200                           205

Arg   Ala   Leu   Ala   Cys   Cys   Cys   Ser   Thr   Asp   Thr   Glu   Ala   Ser   Asn   Val
                      210                           215                           220

Asp   Ala   Val   Ser   Glu   Ile   Thr   Ala   Leu   Ile   Thr   Ala   Gln   Arg   Ala   Tyr
          225                           230                           235                           240

Glu   Met   Asn   Ser   Lys   Val   Ile   Ser   Thr   Ala   Asp   Gln   Met   Leu   Gln   Ala
                            245                           250                           255

Thr   Ser   Gln   Leu   Arg   Ser
                            260
```

(2) INFORMATION FOR SEQ ID NO:8:

(i) SEQUENCE CHARACTERISTICS:
        (A) LENGTH: 264 amino acids
        (B) TYPE: amino acid (C) STRANDEDNESS: single
(D) TOPOLOGY: linear (xi) SEQUENCE DESCRIPTION: SEQ ID NO:8:

| Met | Leu | Ser | Ala | Leu | Tyr | Ser | Gly | Ile | Ser | Gly | Gly | Lys | Asn | Phe | Gln |
| 1 | | | | 5 | | | | | 10 | | | | | 15 | |
| Thr | Lys | Leu | Glu | Val | Ile | Gly | Asn | Asn | Leu | Ala | Asn | Met | Ser | Thr | Val |
| | | | 20 | | | | | 25 | | | | | 30 | | |
| Gly | Thr | Lys | Arg | Gln | Arg | Val | Thr | Phe | Lys | Asp | Met | Val | Ser | Gln | Thr |
| | | 35 | | | | | 40 | | | | | 45 | | | |
| Ile | Ala | Gly | Gly | Ser | Ala | Ala | Gly | Gln | Gly | Ile | Gly | Gly | Thr | Asn | Ser |
| | | 50 | | | | | 55 | | | | | 60 | | | |
| Lys | Gln | Ile | Gly | Leu | Gly | Ser | Ser | Gly | Thr | Ile | Asp | Thr | Ile | His |
| 65 | | | | | 70 | | | | | 75 | | | | 80 |
| Ser | Thr | Ser | Ala | Thr | Gln | Thr | Thr | Gly | Arg | Thr | Lys | Asp | Leu | Ala | Ile |
| | | | | 85 | | | | | 90 | | | | | 95 | |
| Asp | Gly | Asp | Gly | Tyr | Met | Arg | Val | Asp | Thr | Gly | Ser | Gly | Glu | Ala | Tyr |
| | | | 100 | | | | | 105 | | | | | 110 | | |
| Thr | Arg | Ala | Gly | Asn | Phe | Tyr | Leu | Asn | Asn | Thr | Gly | Thr | Leu | Val | Thr |
| | | 115 | | | | | 120 | | | | | 125 | | | |
| Gly | Gly | Ser | Tyr | His | Val | Val | Asn | Met | Asn | Gly | Gly | Thr | Ile | Lys | Ile |
| | 130 | | | | | 135 | | | | | 140 | | | | |
| Pro | Thr | Asp | Ala | Gln | Ser | Phe | Ser | Ile | Gly | Ser | Asp | Ser | Lys | Val | Gln |
| 145 | | | | | 150 | | | | | 155 | | | | | 160 |
| Ile | Val | Asp | Ala | Gln | Gly | Lys | Thr | Gln | Asp | Gly | Gly | Gln | Ile | Gly | Ile |
| | | | | 165 | | | | | 170 | | | | | 175 | |
| Thr | Thr | Phe | Ala | Asn | Ser | Asp | Gly | Leu | Asp | Lys | Ile | Gly | Ser | Asn | Leu |
| | | | 180 | | | | | 185 | | | | | 190 | | |
| Phe | Arg | Glu | Ser | Leu | Asn | Ser | Gly | Thr | Ala | Ser | Glu | Ala | Asn | Gln | Pro |
| | | 195 | | | | | 200 | | | | | 205 | | | |
| Ala | Asp | Gly | Ala | Thr | Ala | Ala | Leu | Lys | Ser | Thr | Tyr | Leu | Glu | Asn | Ser |
| | 210 | | | | | 215 | | | | | 220 | | | | |
| Asn | Val | Asp | Val | Thr | Asp | Glu | Phe | Thr | Glu | Met | Ile | Val | Ala | Gln | Arg |
| 225 | | | | | 230 | | | | | 235 | | | | | 240 |
| Gly | Phe | Gln | Ser | Asn | Ser | Lys | Ile | Val | Ser | Thr | Thr | Asp | Glu | Ile | Leu |
| | | | | 245 | | | | | 250 | | | | | 255 | |
| Gln | Glu | Leu | Val | Asn | Leu | Lys | Arg |
| | | | 260 | | | | |

(2) INFORMATION FOR SEQ ID NO:9:

(i) SEQUENCE CHARACTERISTICS:
(A) LENGTH: 251 amino acids
(B) TYPE: amino acid
(C) STRANDEDNESS: single
(D) TOPOLOGY: linear (xi) SEQUENCE DESCRIPTION: SEQ ID NO:9:

| Met | Asp | His | Ala | Ile | Tyr | Thr | Gly | Met | Ser | Ala | Ala | Ser | Gln | Thr | Leu |
| 1 | | | | 5 | | | | | 10 | | | | | 15 | |
| Asn | Gln | Gln | Ala | Ile | Thr | Ala | Ser | Asn | Ile | Ala | Asn | Ala | Ser | Thr | Pro |
| | | | 20 | | | | | 25 | | | | | 30 | | |
| Gly | Phe | Val | Ala | Gln | Leu | Asn | Ala | Leu | Arg | Ala | Val | Pro | Val | Pro | Gly |
| | | 35 | | | | | 40 | | | | | 45 | | | |
| Lys | Ser | Leu | Ala | Ser | Arg | Thr | Leu | Val | Thr | Ala | Ser | Thr | Pro | Gly | Ala |
| | | 50 | | | | | 55 | | | | | 60 | | | |
| Asp | Met | Thr | Pro | Gly | Gln | Leu | Asp | Tyr | Thr | Ser | Arg | Pro | Tyr | Asp | Val |

|  |  |  |  |  | 65 |  |  |  |  | 70 |  |  |  |  | 75 |  |  |  |  | 80 |
| --- |
|  | Ala | Leu | Gln | Gln | Met | Gly | Trp | Leu | Val | Val | Gln | Ala | Ala | Gly | Gly | Ala |
|  |  |  |  |  | 85 |  |  |  |  | 90 |  |  |  |  | 95 |  |
|  | Glu | Gly | Tyr | Thr | Arg | Asn | Gly | Asn | Ile | Thr | Val | Gly | Pro | Thr | Gly | Gln |
|  |  |  |  | 100 |  |  |  |  | 105 |  |  |  |  | 110 |  |  |
|  | Leu | Thr | Ile | Ala | Gly | His | Pro | Val | Ile | Gly | Glu | Gly | Gly | Pro | Ile | Thr |
|  |  |  |  | 115 |  |  |  |  | 120 |  |  |  |  | 125 |  |  |
|  | Val | Gly | Glu | Gly | Ser | Glu | Ile | Thr | Ile | Ala | Ala | Asp | Gly | Thr | Val | Thr |
|  |  |  | 130 |  |  |  |  | 135 |  |  |  |  | 140 |  |  |  |
|  | Ala | Leu | Asn | Pro | Gly | Asp | Pro | Asn | Thr | Val | Ile | Pro | Val | Gly | Arg |
|  | 145 |  |  |  |  | 150 |  |  |  |  | 155 |  |  |  |  | 160 |
|  | Ile | Lys | Leu | Val | Lys | Ala | Glu | Gly | Asn | Glu | Val | Ala | Arg | Ser | Asp | Asp |
|  |  |  |  |  | 165 |  |  |  |  | 170 |  |  |  |  | 175 |  |
|  | Gly | Leu | Phe | Arg | Leu | Thr | Ala | Glu | Ala | Gln | Ala | Glu | Gln | Gly | Ala | Val |
|  |  |  |  | 180 |  |  |  |  | 185 |  |  |  |  | 190 |  |  |
|  | Val | Ala | Ala | Asp | Pro | Ser | Ile | His | Ile | Met | Ser | Gly | Val | Leu | Glu | Ala |
|  |  |  |  | 195 |  |  |  |  | 200 |  |  |  |  | 205 |  |  |
|  | Ser | Asn | Val | Lys | Pro | Val | Glu | Ala | Met | Ile | Asp | Met | Ile | Ala | Asn | Ala |
|  |  |  |  | 210 |  |  |  |  | 215 |  |  |  |  | 220 |  |  |
|  | Arg | Arg | Phe | Glu | Met | Gln | Met | Lys | Met | Ile | Thr | Ser | Val | Ala | Glu | Ser |
|  | 225 |  |  |  |  | 230 |  |  |  |  | 235 |  |  |  |  | 240 |
|  | Glu | Gly | Arg | Ala | Ala | Gln | Ser | Leu | Ser | Met | Ser |
|  |  |  |  |  | 245 |  |  |  |  | 250 |

( 2 ) INFORMATION FOR SEQ ID NO:10:

( i ) SEQUENCE CHARACTERISTICS:
        ( A ) LENGTH: 260 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

|  | Met | Ile | Ser | Ala | Leu | Trp | Ile | Ala | Lys | Ser | Gly | Leu | Asp | Ala | Gln | Gln |
| --- |
|  | 1 |  |  |  | 5 |  |  |  |  | 10 |  |  |  |  | 15 |  |
|  | Thr | Asn | Met | Glu | Val | Ile | Ala | Asn | Asn | Leu | Ala | Asn | Met | Ser | Thr | Asn |
|  |  |  |  | 20 |  |  |  |  | 25 |  |  |  |  | 30 |  |  |
|  | Gly | Thr | Lys | Arg | Gln | Arg | Ala | Val | Phe | Glu | Asp | Leu | Leu | Tyr | Gln | Thr |
|  |  |  | 35 |  |  |  |  | 40 |  |  |  |  | 45 |  |  |  |
|  | Ile | Arg | Gln | Pro | Gly | Ala | Gln | Ser | Ser | Glu | Gln | Gly | Asn | Ile | Pro | Thr |
|  |  | 50 |  |  |  |  | 55 |  |  |  |  | 60 |  |  |  |  |
|  | Gly | Leu | Gln | Ile | Gly | Thr | Gly | Val | Lys | Ala | Val | Ala | Thr | Glu | Arg | Leu |
|  | 65 |  |  |  |  | 70 |  |  |  |  | 75 |  |  |  |  | 80 |
|  | His | Ser | Gln | Gln | Gly | Leu | Thr | Gln | Thr | Asn | Asn | Ser | Lys | Asp | Val | Ala |
|  |  |  |  |  | 85 |  |  |  |  | 90 |  |  |  |  | 95 |  |
|  | Ile | Lys | Gly | Gln | Gly | Tyr | Met | Pro | Val | Met | Leu | Pro | Ser | Gly | Glu | Ser |
|  |  |  |  | 100 |  |  |  |  | 105 |  |  |  |  | 110 |  |  |
|  | Ala | Tyr | Thr | Arg | Asp | Gly | Ser | Phe | Gly | Val | Asn | Gly | Asn | Gly | Gln | Leu |
|  |  |  |  | 115 |  |  |  |  | 120 |  |  |  |  | 125 |  |  |
|  | Val | Thr | Ala | Gly | Gly | Phe | Gln | Val | Gln | Pro | Ala | Ile | Thr | Ile | Pro | Ala |
|  |  |  | 130 |  |  |  |  | 135 |  |  |  |  | 140 |  |  |  |
|  | Asn | Ala | Leu | Ser | Ile | Thr | Ile | Gly | Arg | Asp | Gly | Val | Val | Gln | Val | Thr |
|  | 145 |  |  |  |  | 150 |  |  |  |  | 155 |  |  |  |  | 160 |
|  | Gln | Gln | Gly | Gln | Ala | Ala | Pro | Val | Thr | Val | Gly | Gln | Leu | Asn | Leu | Thr |
|  |  |  |  |  | 165 |  |  |  |  | 170 |  |  |  |  | 175 |  |
|  | Thr | Phe | Met | Asn | Asp | Thr | Gly | Leu | Glu | Ser | Ile | Gly | Glu | Asn | Leu | Phe |

-continued

| | | | | | | | 180 | | | | 185 | | | 190 | |
|---|---|---|---|---|---|---|---|---|---|---|---|---|---|---|---|
| Ile | Glu | Thr | Gln | Ser | Ser | Gly | Ala | Ala | Asn | Glu | Ser | Thr | Pro | Ala | Leu |
| | | 195 | | | | | 200 | | | | 205 | | | | |
| Asn | Ala | Ala | Ala | Leu | Leu | Tyr | Gln | Thr | Tyr | Val | Glu | Thr | Ser | Asn | Val |
| | 210 | | | | | 215 | | | | | 220 | | | | |
| Asn | Val | Ala | Ser | Glu | Leu | Val | Asn | Met | Ile | Gln | Val | Gln | Arg | Ala | Tyr |
| 225 | | | | | 230 | | | | | 235 | | | | | 240 |
| Glu | Ile | Asn | Ser | Lys | Ala | Val | Ser | Thr | Thr | Asp | Gln | Met | Leu | Gln | Lys |
| | | | | 245 | | | | | 250 | | | | | 255 | |
| Leu | Thr | Gln | Leu | | | | | | | | | | | | |
| | | | 260 | | | | | | | | | | | | |